US 9,980,925 B2

(12) United States Patent
Morad et al.

(10) Patent No.: US 9,980,925 B2
(45) Date of Patent: May 29, 2018

(54) XANTHOHUMOL IN ANTIARRYTHMIC APPLICATIONS

(71) Applicant: University of South Carolina, Columbia, SC (US)

(72) Inventors: Martin Morad, Charleston, SC (US); Lars Cleemann, Charleston, SC (US); Juan Jose Arnaiz-Cot, Charleston, SC (US)

(73) Assignee: University of South Carolina, Columbia, SC (US)

( * ) Notice: Subject to any disclaimer, the term of this patent is extended or adjusted under 35 U.S.C. 154(b) by 35 days.

(21) Appl. No.: 15/496,022

(22) Filed: Apr. 25, 2017

(65) Prior Publication Data

US 2017/0304220 A1    Oct. 26, 2017

Related U.S. Application Data

(60) Provisional application No. 62/327,120, filed on Apr. 25, 2016.

(51) Int. Cl.
*A61K 31/12* (2006.01)
*A61K 31/137* (2006.01)

(52) U.S. Cl.
CPC ............ *A61K 31/12* (2013.01); *A61K 31/137* (2013.01)

(58) Field of Classification Search
CPC .............................. A61K 31/12; A61K 31/137
See application file for complete search history.

(56) References Cited

PUBLICATIONS

Hussong et al., Molecular Nutrition and Food Research, 2005, vol. 49, pp. 861-867.*
Cleemann L, Morad M (1991). Role of Ca+ channel in cardiac excitation-contraction coupling in the rat: evidence from Ca2+ transients and contraction. *The Journal of physiology* 432: 283-312.
Cleemann L, Wang W, Morad M (1998). Two-dimensional confocal images of organization, density, and gating of focal Ca2+ release sites in rat cardiac myocytes. Proceedings of the National Academy of Sciences of the United States of America 95(18): 10984-10989.
Dorn C, Heilmann J, Hellerbrand C (2012). Protective effect of xanthohumol on toxininduced liver inflammation and fibrosis. International journal of clinical and experimental pathology 5(1): 29-36.
Dorn C, Massinger S, Wuzik A, Heilmann J, Hellerbrand C (2013). Xanthohumol suppresses inflammatory response to warm ischemia-reperfusion induced liver injury. *Experimental and molecular pathology* 94(1): 10-16.
Drenzek JG, Seiler NL, Jaskula-Sztul R, Rausch MM, Rose SL (2011). Xanthohumol decreases Notch1 expression and cell growth by cell cycle arrest and induction of apoptosis in epithelial ovarian cancer cell lines. Gynecologic oncology 122(2): 396-401.

(Continued)

*Primary Examiner* — Savitha M Rao
(74) *Attorney, Agent, or Firm* — Dority & Manning, P.A.

(57) ABSTRACT

Methods for modulating $Ca^{2+}$ signaling in cardiac myocytes by use of xanthohumol are described. Xanthohumol can suppress $Ca^{2+}$ signaling by suppressing spontaneous activity of the RyR2 receptor. Delivery of xanthohumol to a cardiocyte can be utilized in treatment of cardiac arrhythmia.

16 Claims, 15 Drawing Sheets

(56) References Cited

PUBLICATIONS

Haviland S, Cleemann L, Kettlewell S, Smith GL, Morad M (2014). Diversity of mitochondrial Ca(2)(+) signaling in rat neonatal cardiomyoeytes: evidence from a genetically directed Ca(2)(+) probe, mitycam-E31Q. Cell calcium 56(3): 133-146.

Hirata H, Yimin, Segawa S, Ozaki M, Kobayashi N, Shigyo T, et al. (2012). Xanthohumol prevents atherosclerosis by reducing arterial cholesterol content via CETP and apolipoprotein E in CETP-transgenic mice. PloS one 7(11): e49415.

Mitra R, Morad M (1985). A uniform enzymatic method for dissociation of myocytes from hearts and stomachs of vertebrates. The American journal of physiology 249(5 Pt 2): H1056-1060.

Suh KS, Rhee SY, Kim YS, Lee YS, Choi EM (2013). Xanthohumol modulates the expression of osteoclast-specific genes during osteoclastogenesis in RAW264.7 cells. Food and chemical toxicology : an international journal published for the British Industrial Biological Research Association 62: 99-106.

Weiskirchen R, Mahli A, Weiskirchen S, Hellerbrand C (2015). The hop constituent xanthohumol exhibits hepatoprotective effects and inhibits the activation of hepatic stellate cells at different levels. Frontiers in physiology 6: 140.

Yang M, Li N, Li F, Zhu Q, Liu X, Han Q, et al. (2013). Xanthohumol, a main prenylated chalcone from hops, reduces liver damage and modulates oxidative reaction and apoptosis in hepatitis C virus infected Tupaia belangeri. International immunopharmacology 16(4): 466-474.

Yuan Y, Qiu X, Nikolic D, Chen SN, Huang K, Li G, et al. (2014). Inhibition of human cytochrome P450 enzymes by hops (*Humulus lupulus*) and hop prenylphenols. European journal of pharmaceutical sciences : official journal of the European Federation for Pharmaceutical Sciences 53: 55-61.

Yui K, Kiyofuji A, Osada K (2014). Effects of xanthohumol-rich extract from the hop on fatty acid metabolism in rats fed a high-fat diet. Journal of oleo science 63(2): 159-168.

Zamzow DR, Elias V, Legette LL, Choi J, Stevens JF, Magnusson KR (2014). Xanthohumol improved cognitive flexibility in young mice. Behavioural brain research 275: 1-10.

\* cited by examiner

XANTHOHUMOL IN ANTIARRYTHMIC APPLICATIONS

CROSS REFERENCE TO RELATED APPLICATION

This application claims filing benefit of U.S. Provisional Patent Application Ser. No. 62/327,120 having a filing date of Apr. 25, 2016 entitled "Xanthohumol Modulates Calcium Signaling in Rat Ventricular Myocytes: Possible Antiarrythmic Properties," which is incorporated herein by reference.

STATEMENT REGARDING FEDERALLY SPONSORED RESEARCH OR DEVELOPMENT

This invention was made with government support under Grant No. HL 16152 awarded by the National Institutes of Health. The government has certain rights in the invention.

BACKGROUND

Cardiac arrhythmia is a major cause of mortality in cardiovascular pathologies. Aberrancies in cardiac $Ca^{2+}$ signaling have been associated with development of arrhythmia. For instance, it has been found that leaky ryanodine receptors elevate local $Ca^{2+}$ concentrations causing membrane depolarizations that trigger arrhythmias. Increases in frequency of $Ca^{2+}$ sparks that trigger $Ca^{2+}$ waves are known to activate depolarizing currents responsible for early or late after-depolarizations and arrhythmias. Due to such findings, $Ca^{2+}$ signaling has been a primary target of antiarrhythmic pharmacotherapy. In fact, inhibition of the spontaneous release of $Ca^{2+}$ (e.g., via leaky ryanodine receptors) is proposed to be critical in the pharmacotherapy of arrhythmias, as reported recently for clinical use of flecainide.

The regulation of $Ca^{2+}$ release from the sarcoplasmic reticulum (SR) is mediated not only by binding of $Ca^{2+}$ to ryanodine receptor 2 (RyR2), but also by a host of regulatory proteins that include calmodulin, protein kinase A, FK506-binding protein (FKBP12.6), $Ca^{2+}$/calmodulin-dependent protein kinase II, protein phosphatases (calcineurin), and junctional and luminal SR proteins junctin, triadin, and calsequestrin. In addition, mitochondrial-derived reactive oxygen species (ROS) have been reported to modulate RyR2-mediated $Ca^{2+}$ spark activity, supporting the possibility that local control of SR $Ca^{2+}$ release is regulated partially by mitochondrial ROS production. In ischemia-reperfusion-induced arrhythmias, experimental evidence also suggests deleterious effects arising from mitochondrial $Ca^{2+}$ overload, ROS generation, and opening of permeability transition pores that leads to overactive RyR2 activity, causing local membrane depolarizations. It has been suggested that these depolarizations propagate from cell to cell and can be effectively suppressed by free oxygen radical scavengers.

Xanthohumol, a prenylated chalcone, is one of the principal flavonoids present in hop plant cone extracts. Flavonoids have been reported to have therapeutic effects as an antiproliferative in human breast cancer, colon cancer, and ovarian cancer, and in preventing cancerous cell growth through inhibition of cytochrome P450 enzymes. Xanthohumol has also been suggested to counteract low-density lipoprotein-induced oxygen-damaging effects, improve neuronal plasticity, and produce therapeutic effects against arteriosclerosis and osteoporosis.

Unfortunately, a host of drugs targeted to sarcolemmal $Na^+$, $Ca^{2+}$, and $K^+$ channels for antiarrhythmic pharmocotherapy have had limited clinical success. What is needed in the field are agents that can be effective in reducing the cardiomyocyte Ca2+ leak that leads to arrhythmia.

SUMMARY

According to one embodiment, disclosed is a composition for treatment of arrhythmia comprising xanthohumol. Also disclosed are methods for modulating $Ca^{2+}$ signaling in cardiac myocytes, and in one particular embodiment modulating $Ca^{2+}$ signaling by suppressing spontaneous activity of a RyR2 receptor. The method can include delivering xanthohumol to a myocyte, and in one particular embodiment a cardiac myocyte, comprising the RyR2 receptor. In one embodiment, a method can be utilized in treatment of cardiac arrhythmia.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 4 illustrates that xanthohumol reduces the number of spontaneous $Ca^{2+}$ sparks in cells challenged with low $K^+$ (0 mM) (A-C) and of aberrant $Ca^{2+}$ transients in field-stimulated cells (D-F). (A) Comparison of frequency and amplitude of $Ca^{2+}$ sparks measured in Fluo-4 AM-incubated rat ventricular cells perfused at 25° C. with control solution (5.4 mM $K^+$), after 3-minute exposure to reduced $K^+$ (1.5 mM $K^+$), and 3 minutes later after addition of 50 nM xanthohumol. (B) Similar recordings in a cell pre-incubated with 10 nM xanthohumol for 30 minutes. (C) Histogram showing suppression by xanthohumol (50-100 nM) of average number of sparks under these conditions (one-way analysis of variance with Tukey's multiple comparison test, *P<0.05, P<0.01). (D-F) Effect of 50-100 nM xanthohumol on cellular $Ca^{2+}$ transients ($\Delta F/F_0$, Fluo-4 AM) in ventricular cardiomyocytes at 35° C. in control solution. (D) Stimulated $Ca^{2+}$ transients followed at irregular intervals by secondary $Ca^{2+}$ releases suggesting early after depolarizations. (E) Disappearance of irregular $Ca^{2+}$ releases 2.5 minutes after addition of 100 nM xanthohumol. (F) Histograms showing that xanthohumol blocks aberrant secondary $Ca^{2+}$ release events (Events) without decreasing the amplitude of electrically stimulated cellular $Ca^{2+}$ transients ($\Delta F/F_0$, paired t test, *P<0.001). (C and F) Sample sizes are shown next to each bar.

Figure 5:
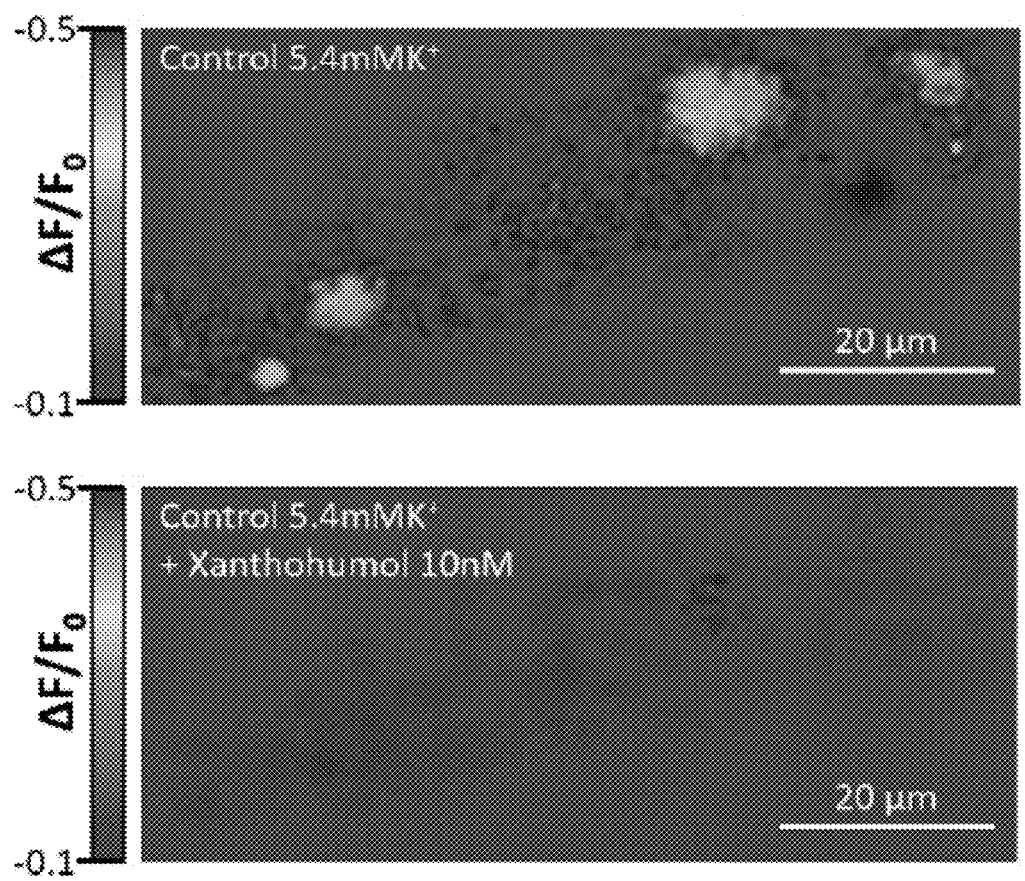

FIG. 5 includes images from videos showing suppression of $Ca^{2+}$ sparks in rat ventricular cell by 10 nM xanthohumol. EPI-fluorescence imaging at 23 frames/sec. Recordings at 25° C. from rat ventricular cell incubated with Fluo-4AM.

Figure 6:
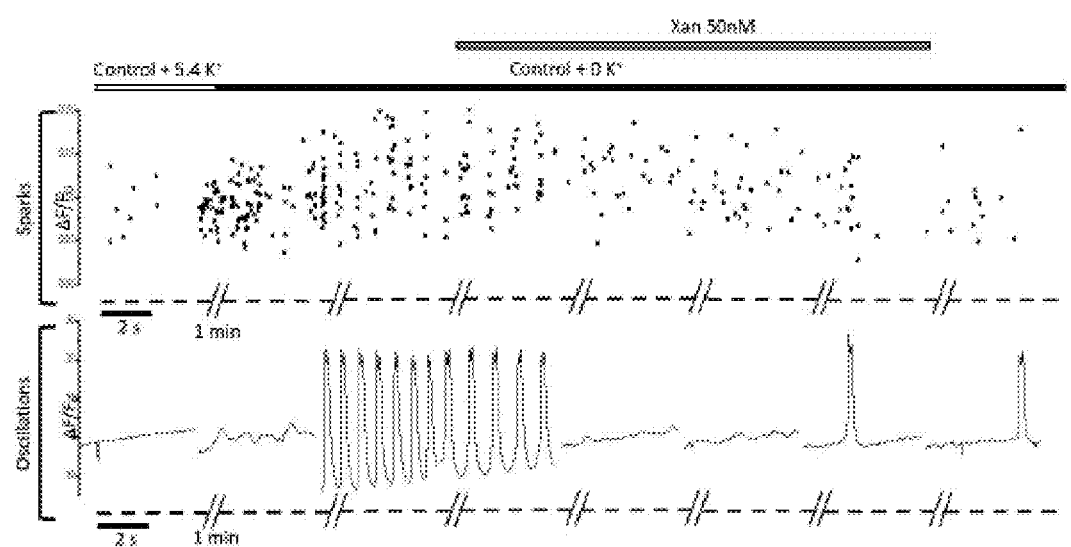

FIG. 6 presents the enhanced $Ca^{2+}$ spark generation (top) and the spontaneous pacing (bottom) produced by $K^+$ withdrawal in a rat ventricular cell are suppressed by 50 nM xanthohumol. Continuous whole-cell measurements of Fluo-4AM fluorescence in a rat ventricular cell.

Figure 7:
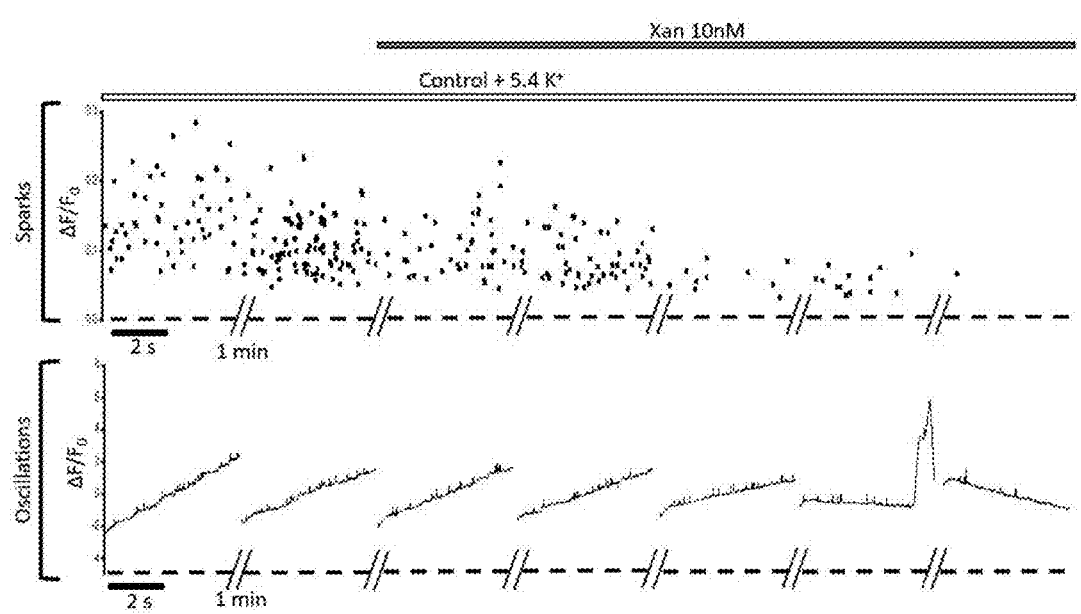

FIG. 7 demonstrates xanthohumol (10 nM) suppresses the rate of $Ca^{2+}$ spark generation in those rat ventricular cells where such activity occurs spontaneously under control conditions (5.4 mM $K^+$). The upper panel shows the amplitude and timing of each $Ca^{2+}$ spark above detection threshold ($\Delta F/F_0$>0.05). The lower panel shows that the suppression of $Ca^{2+}$ sparks by xanthohumol was accompanied by a reversal of the concurrent increase in baseline $Ca^{2+}$ as detected by a rise in baseline fluorescence. Epi-fluorescence imaging of Fluo-4 at 60 Hz was performed for 5 sec every minute.

Figure 8:
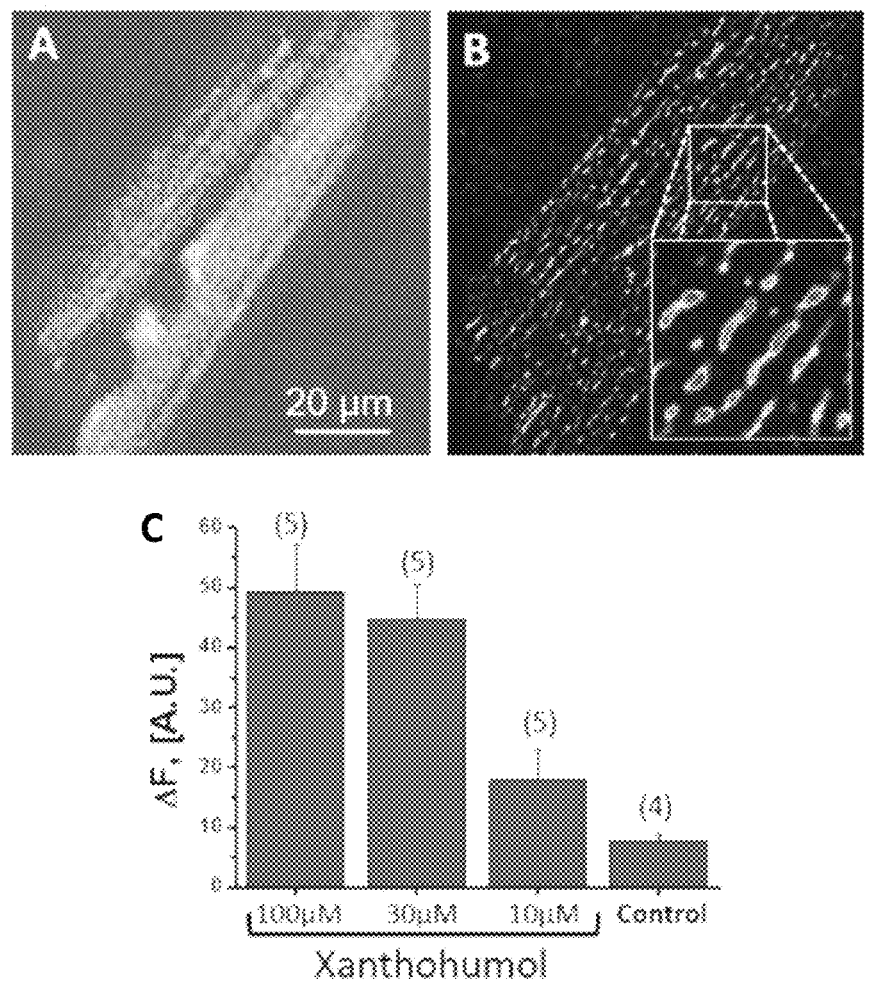

FIG. 8 illustrates mitochondrial uptake of xanthohumol. Fluorescence of xanthohumol ($\lambda_{ex}$=488 nm, $\lambda_{em}$>515 nm) measured confocally in freshly dissociated mouse ventricular cells after 10 min incubation. A, B: Unfiltered (A) and contrast-enhanced fluorescence images (B) measured with 30 µM xanthohumol showing mitochondrial distribution with longitudinal bands and concentration near nuclei. C: Dose dependence increase in fluorescence ($\Delta F$) measured with identical settings in 5 cells at each concentration.

Figure 9:
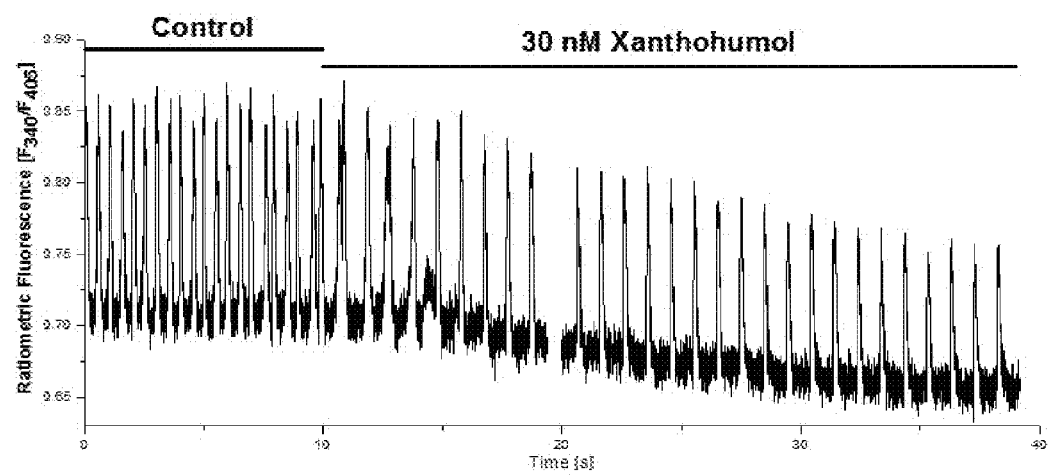

FIG. 9 illustrates the rapid suppression (<10 s) of aberrant cellular $Ca^{2+}$ transients by 30 nM xanthohumol in an electrically stimulated (1 Hz) rat ventricular cell. Under control conditions the cell produced spontaneous $Ca^{2+}$ transients occurring between the stimulated beats. The suppression of the spontaneous $Ca^{2+}$ transients by xanthohumol was accompanied by a decline in baseline calcium as evidenced by the slowly falling baseline fluorescence. Continuous whole-cell measurements of Fluo-4AM fluorescence in a rat ventricular cell at 25° C.

Figure 10:
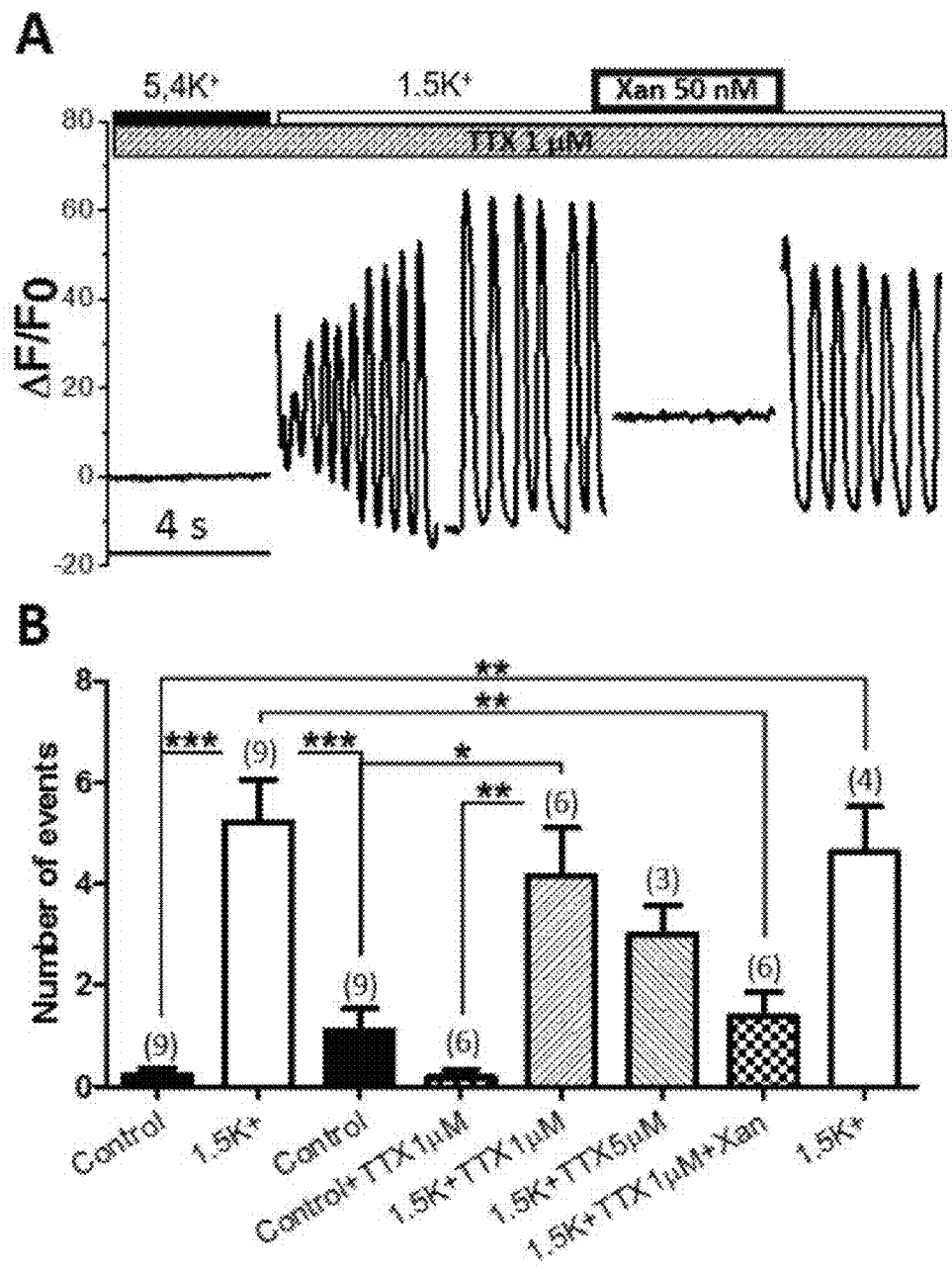

FIG. 10 panel A shows the signal produced by a cell previously incubated with Fluo4 AM using confocal microscopy. Perfusion of 1.5 mM $K^+$ produced oscillatory activity that was not suppressed by TTX 1 µM. Under these conditions the perfusion of Xanthohumol 50 nM produced a significant difference with respect to the oscillatory effect produced by 1.5 µM $K^+$ (p<0.01) (right, panel A). After washing out the xanthohumol, perfusion of 1.5 mM $K^+$ recovers the spontaneous activity. On panel B the histogram shows the number of oscillatory events recorded for a period of 4 s. Statistics based on one-way analysis of variance with the posttest Bonferroni's multiple comparison test at 25°.

Figure 11:
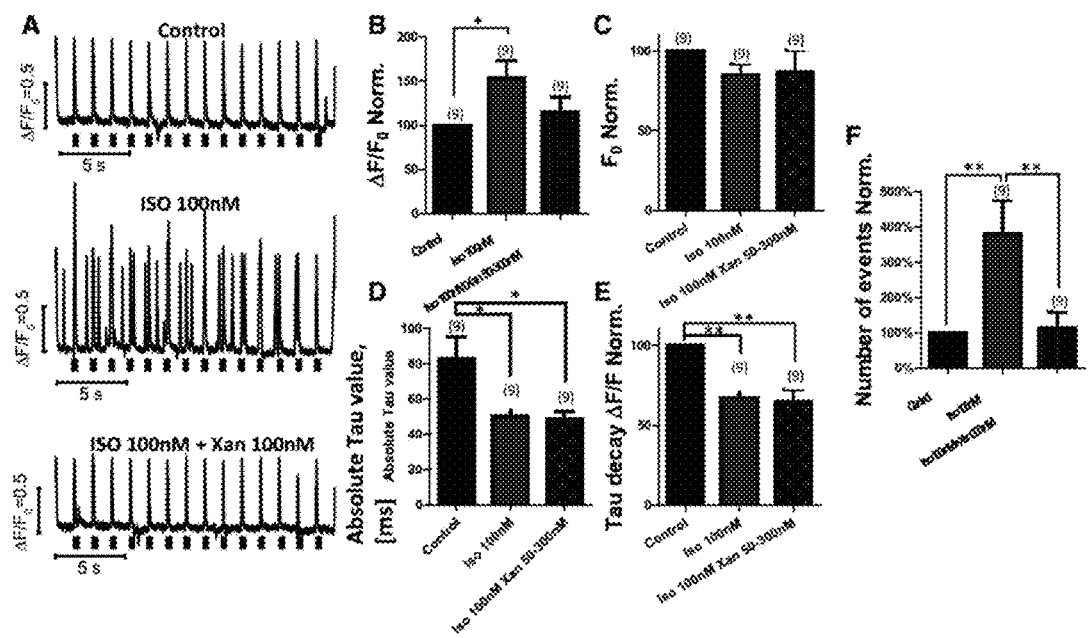

FIG. 11 illustrates that xanthohumol reduces the spontaneous activity triggered by isoproterenol (100 nM) (A and F) with little or no change in the peak (B) $\Delta F/F_0$ or basal $Ca^{2+}$ signals (C, $F_0$) or the directly measured (D) or normalized (E) time constant of decay of the $Ca^{2+}$ transient (Tau) produced by electrical stimulation (0.75 Hz at 35° C.). (A) Effect of isoproterenol and isoproterenol plus xanthohumol on fluo-4 AM-incubated cells that did not show spontaneous activity under control conditions. The number of spontaneous events was increased in the presence of isoproterenol but recovered normal values in the presence of xanthohumol (***P<0.005, repeated measures analysis of variance and Newman-Keuls multiple comparison test) (E). (B, C, and E) Analysis of normalized values of $\Delta F/F_0$, $F_0$, Tau of electrically stimulated $Ca^{2+}$ transients. Isoproterenol at 100 nM significantly increased $\Delta F/F0$ (P=0.0464, repeated measures analysis of variance, and Tukey's multiple comparison test). Tau was significantly reduced by isoproterenol, and this tendency was not modified when xanthohumol was added (P, 0.005, repeated measures analysis of variance and Tukey's multiple comparison test). (B-E) Sample sizes are shown next to each bar.

Figure 12:
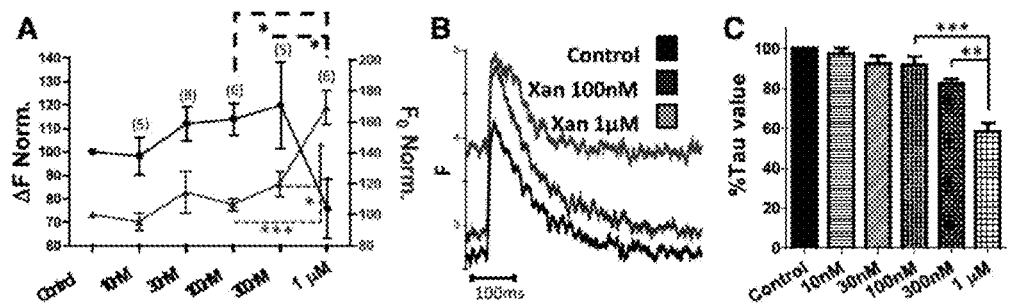

FIG. 12 presents concentration dependence effect of xanthohumol on ventricular cardiomyocyte electrically stimulated cells (0.5 Hz) at 35° C. (A) Effect of xanthohumol measured after 5-minute exposure to different concentrations. dF and $F_0$ were normalized with respect to control. To avoid possible cumulative effects of xanthohumol, one concentration was used for each cell or the next concentration used in the same cell was 10 times higher. (B) Original traces of the fluorescence signal during a single electrical pulse under control conditions and in the presence of 100 nM and 1 µM xanthohumol. (C) Xanthohumol significantly reduced Tau at concentrations over 300 nM (one-way analysis of variance and Tukey's post hoc test). Sample sizes are shown next to each data point (A) or bar (C).

Figure 13:
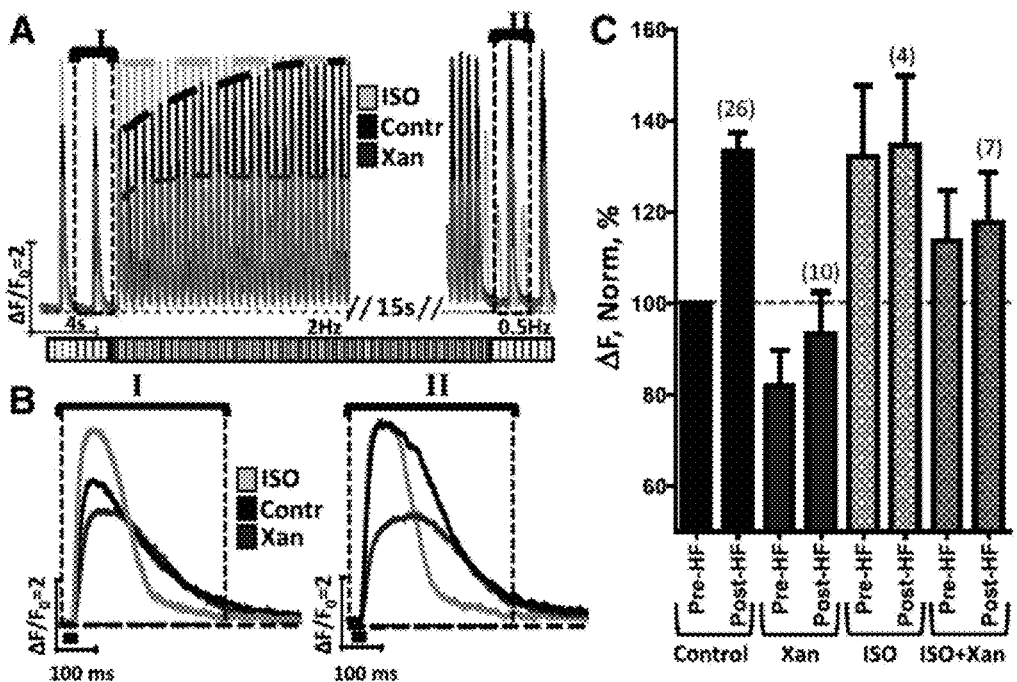

FIG. 13 demonstrates xanthohumol suppresses the increase in the $Ca^{2+}$ release produced by rapid electrical stimulation (2 versus 0.5 Hz) for 1 minute. (A and B) Superimposed traces of fluorescence during low and high rates of stimulation under control conditions and after exposure to xanthohumol (50 nM) or isoproterenol (100 nM). (C) Normalized amplitudes ($\Delta F$) of $Ca^{2+}$ transients measured pre (I) and post (II) rapid pacing under control conditions and in presence of xanthohumol (50 nM) and isoproterenol (100 nM) applied separately or together. Fluo-4 AM-incubated cells at 35° C. (C) Sample sizes are shown next to each bar.

Figure 14:
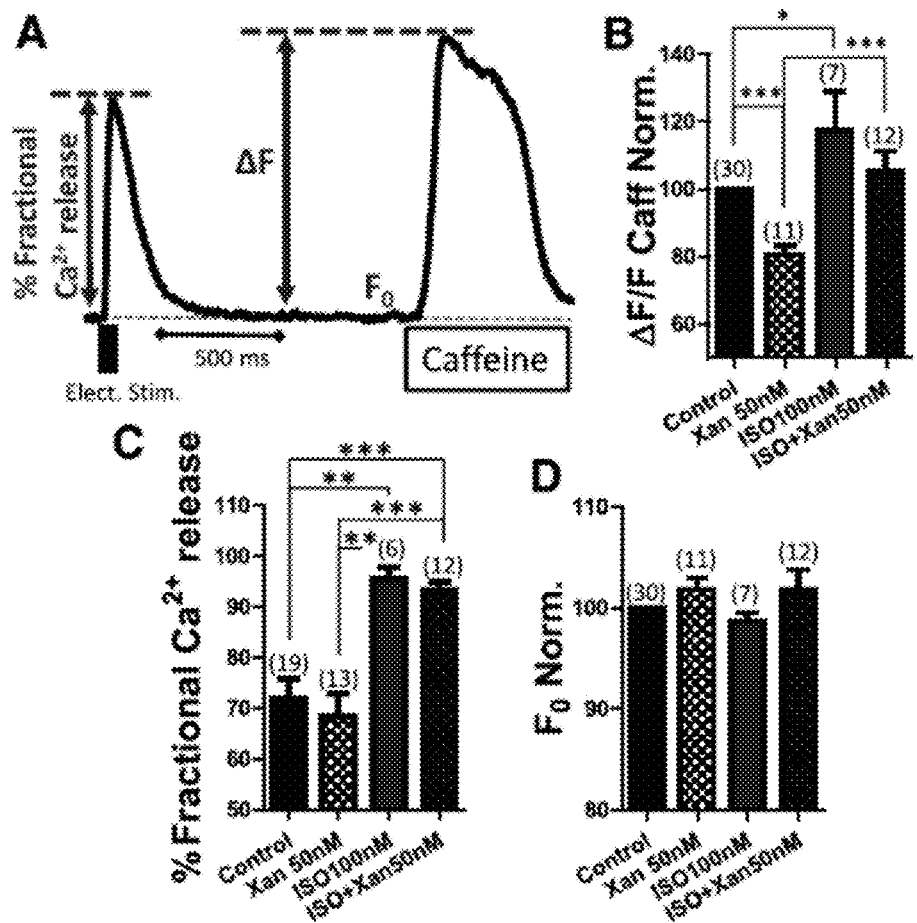

FIG. 14 illustrates the fraction of the caffeine-releasable $Ca^{2+}$ pool that was released by electrical stimulation was enhanced by isoproterenol (100 nM), but was not influenced by xanthohumol (50 nM). (A) $Ca^{2+}$ transients evoked by electrical stimulation ($\Delta F_{Stim}$) and by exposure to caffeine (2.5 mM for 1 second, $\Delta F_{Caff}$). (B-D) Average values of the caffeine-releasable $Ca^{2+}$ pool normalized to control conditions (B, $\Delta F_{Caff}$), the fractional $Ca^{2+}$ release (C, $\Delta F_{Stim}/\Delta F_{Caff}$, and the normalized baseline fluorescence (D, $F_0$). Fluo-4 AM-incubated cells paced at 0.5 Hz at 35° C. One-way analysis of variance and Tukey's test. (B-D) Sample sizes are shown next to each bar.

Figure 15:
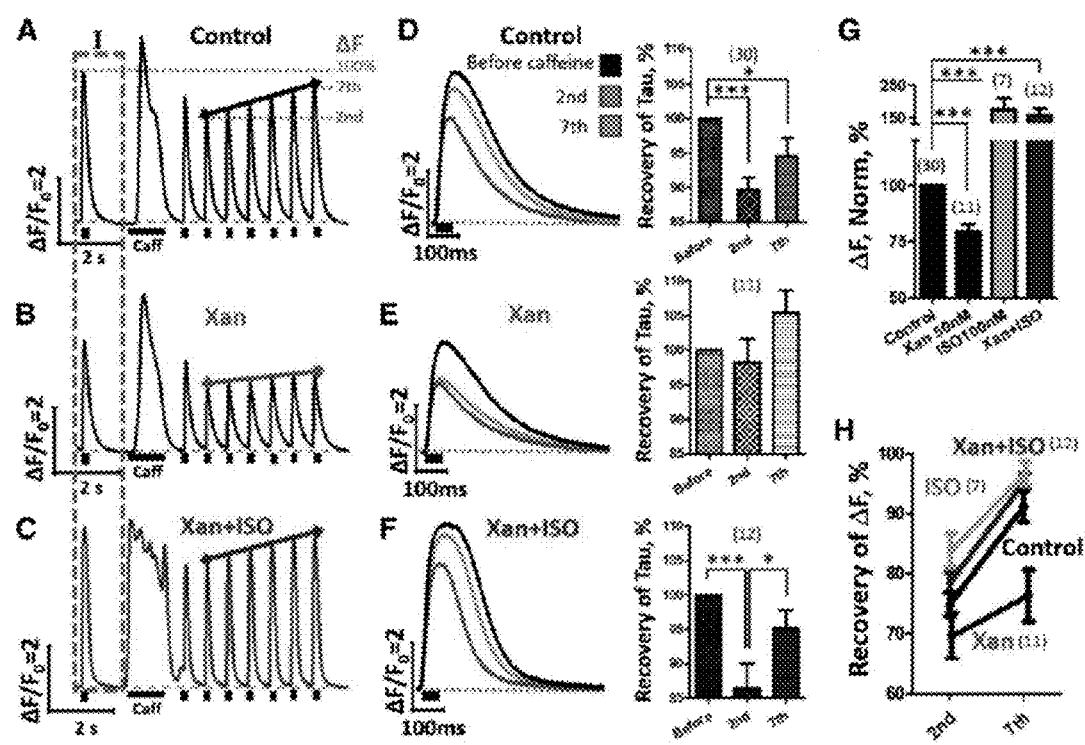

FIG. 15 demonstrates the modulatory effect of xanthohumol (50 nM) and isoproterenol (100 nM) on the recovery at 35° C. of the amplitude and kinetics of stimulated $Ca^{2+}$ transients (1.5 Hz) following caffeine-induced (2.5 mM, 1 second) $Ca^{2+}$ release. The cells were equilibrated for 1.5 minutes between test runs while stimulating at 0.5 Hz. (A-C). Sample records showing $Ca^{2+}$ transient evoked by a last stimulus before caffeine (I), caffeine, and seven stimuli after caffeine recorded under control conditions (A), in presence of xanthohumol (B), and with co-application of this drug with isoproterenol (ISO) (C). (D-F) Records with expanded time base showing second and seventh post-caffeine $Ca^{2+}$ transients superimposed on last pre-caffeine $Ca^{2+}$ transient and average values quantifying the recovery of Tau toward its pre-caffeine value. (G) Amplitude of $Ca^{2+}$ transients in the presence of xanthohumol, isoproterenol, or both normalized relative to drug-free control conditions. (H) Recovery of the amplitude of post-caffeine-stimulated $Ca^{2+}$ transients toward the pre-caffeine value.

Figure 16:
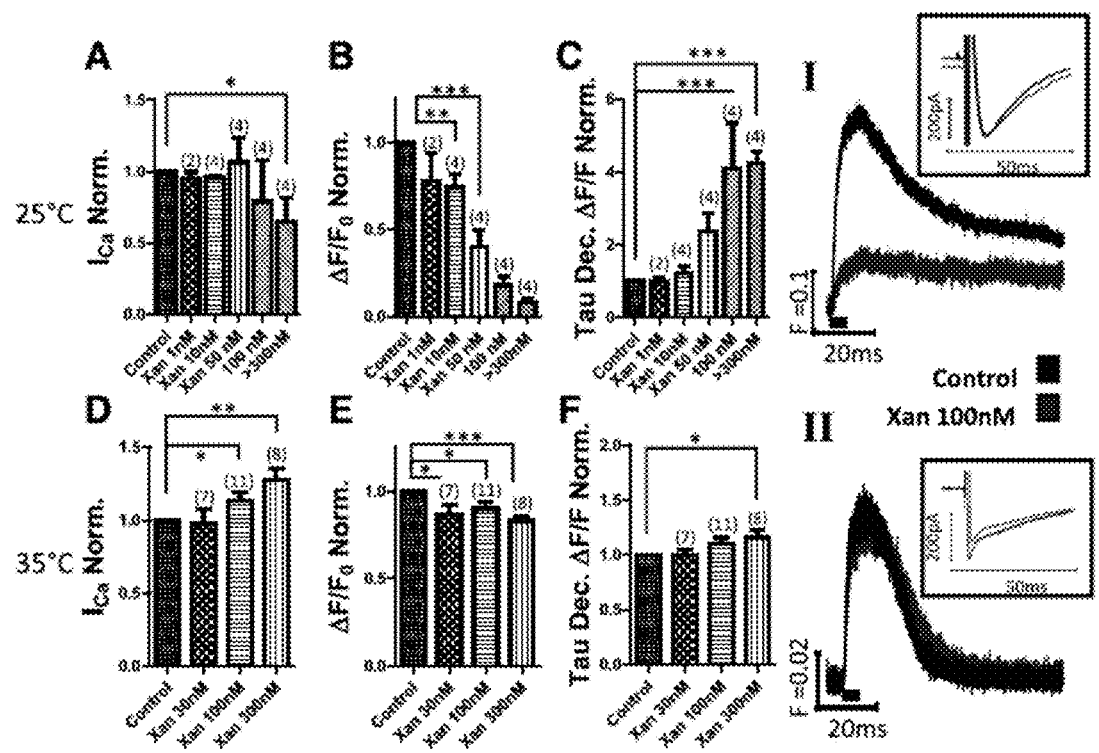

FIG. 16 demonstrates the temperature dependence of the xanthohumol effect at different concentrations in voltage-clamped cells (–50 mV) depolarized for 100 ms to 0 mV every 30 seconds. (A-F) Histograms showing normalized average of $I_{Ca}$ (A and D), $\Delta F/F_0$ (B and E; Fluo-4 AM), and Tau (C and F) at different temperatures (A-C, 25° C. versus E-F, 35° C.) and concentrations of xanthohumol. (I and II) Sample records at 25° C. and 35° C., respectively, voltage-clamp protocol (top), $I_{Ca}$ (middle), and $Ca^{2+}$ transients (bottom) in the absence and presence of 100 nM xanthohumol. Insets show expanded current traces. Repeated measures analysis of variance, Turkey's multiple comparison test, and t test.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to compositions and methods for the utilization of xanthohumol in modulation of cardiac $Ca^{2+}$ signaling. More specifically, disclosed methods are directed to the utilization of xanthohumol in suppression of aberrant spontaneous activity of the myocyte RyR2 as may lead to cardiac arrhythmia. As mentioned previously, xanthohumol is an antioxidant extracted from hops, and has been known to exhibit therapeutic effects in other pathologies, but has previously been unrecognized for antiarrhythmic efficacy.

In general, methods can include contacting a myocyte with an amount of xanthohumol in a suitable concentration (e.g., about 1 mM or less, or about 1 μM or less in some embodiments). Upon interaction with xanthohumol, the frequency of spontaneously occurring $Ca^{2+}$ sparks in the cell can be reduced (e.g., up to threefold in some embodiments) as can the frequency of $Ca^{2+}$ waves. For instance, the frequency of spontaneously occurring $Ca^{2+}$ sparks and/or waves can be reduced through contact of myocytes with xanthohumol at a contact concentration of from about 5 nM to about 50 nM.

Reduction in $Ca^{2+}$ sparks and/or $Ca^{2+}$ waves can take place in both healthy, e.g., control, myocytes as well as in cells subjected to $Ca^{2+}$ overload conditions. $Ca^{2+}$ overload (i.e., increase of the cytosolic $Ca^{2+}$) can occur by increasing the influx of $Na^+$ and $Ca^{2+}$ via the sarcolemmal $Na^+$ channels, $Ca^{2+}$ channels, and the Na/Ca exchanger, (NCX). $Ca^{2+}$ overload brought about in any fashion can be moderated by use of xanthohumol. For instance, $Ca^{2+}$ overload conditions can include, without limitation, low $K^+$ environment (e.g., exposure to low $K^+$ solution), electrical stimulation (e.g., exposure to periods of high frequency electrical stimulation), exposure to cardiac stimulating chemicals such as isoproterenol or other β-adrenergic agonists, caffeine, etc., or combinations of conditions. Accordingly, in one embodiment, treatment methods can be directed to modifying the effect of a $Ca^{2+}$ overload condition (a compound exposure and/or an environmental condition) in a myocyte through delivery of xanthohumol to the cell.

In one embodiment, xanthohumol can be utilized to reduce the rate of relaxation of $Ca^{2+}$ transients, and beneficially can do so without suppressing $Ca^{2+}$ current ($I_{Ca}$). In one embodiment, the $Ca^{2+}$ transient relaxation effect can be obtained through contact of a cell with xanthohumol in a concentration of from about 50 nm to about 100 nM. $Ca^{2+}$ transients as may be effected can be spontaneous or can be triggered, for instance electrically or by use of a stimulant, e.g., caffeine, as is known.

Exposure of a cell to a β-adrenergic agonist such as isoproterenol can mitigate this relaxation effect. For instance, exposure of a cell to isoproterenol can fully reverse the suppressive effects of xanthohumol on $Ca^{2+}$ transients and its relaxation. Moreover, in cells pre-exposed to isoproterenol, $Ca^{2+}$ transient suppressive effects of xanthohumol can be undetected.

The xanthohumol effect on the rate of decay of $Ca^{2+}$ transients appears to be more pronounced at lower temperatures, e.g., about 25° C., than at physiologic temperatures. Thus, both higher temperatures (e.g., about 35° C.) and β-adrenergic agonists (e.g., isoproterenol) can reduce or override the suppressive effects of xanthohumol on the rate of relaxation of $Ca^{2+}$ transients. Interestingly however, xanthohumol-treated myocytes, even in the presence of isoproterenol, can be resistant to triggered spontaneous beats.

It is noteworthy that xanthohumol-induced reduction in spontaneous activity of a myocyte can occur without a significant effect on the magnitude or kinetics of the $Ca^{2+}$ currents. This suggests that xanthohumol does not significantly modify the normal CICR-mediated $Ca^{2+}$ signaling but can suppress spontaneously generated $Ca^{2+}$ oscillations, perhaps secondary to its antioxidant properties.

In one embodiment, xanthohumol can be utilized to suppress $Ca^{2+}$ content of the SR and its rate of refilling and recirculation, for instance after caffeine-induced depletion. Because xanthohumol can also slow the rate of decay of electrically triggered $Ca^{2+}$ transients, for instance following washout of caffeine, it is believed that SR uptake rate of $Ca^{2+}$ may be compromised by the presence of xanthohumol.

As illustrated in the Examples section, it appears that xanthohumol can accumulate in mitochondria. This, combined with its known strong antioxidant property, may allow for xanthohumol to effectively buffer oxygen radicals generated at their source in mitochondria during periods of over-activity and $Ca^{2+}$ overload. The mitochondrial localization of xanthohumol and its efficacy at nanomolar concentrations, is believed to arise from possible drug accumulations at the sites of ROS generation. Without wishing to be bound to any particular theory, it is believed that significant differences in the efficacy of various antioxidants vis-a-vis their antiarrhythmic activities arise, at least in part, from their intracellular compartmentation, and as such, xanthohumol may be particularly effective in an antiarrythmic application.

In arrhythmia and heart failure, significant increases in cytosolic $Na^+$ and $Ca^{2+}$ are often reported, which may accelerate mitochondrial $Ca^{2+}$ turnover, causing generation of ROS and possibly loss of mitochondrial redox potential, decrease in ATP levels, and opening of sarcolemmal KATP channels. In this respect, xanthohumol may have a particularly beneficial therapeutic effect, as its accumulation in the mitochondria can allow buffering of ROS at the source, thus prevent the oxidizing effects of ROS on rendering RyR2 leaky that might lead to lethal arrhythmogenesis.

The stabilizing effects of xanthohumol on the frequency of spontaneously triggered $Ca^{2+}$ sparks and $Ca^{2+}$ waves combined with its antioxidant properties, $Ca^{2+}$ transient relaxation effects, and suppression of $Ca^{2+}$ content of the SR, all with lack of significant effects on $Na^+$ and $Ca^{2+}$ channels and without altering $Ca^{2+}$ sensitivity of RyR2, can provide this compound with clinically desirable antiarrhythmic properties.

The present disclosure may be better understood with reference to the Examples set forth below.

EXAMPLE

Methods
Isolation of Rat Cardiac Myocytes

Cardiac myocytes from the ventricles of male Sprague-Dawley rats were isolated, according to standard protocols. Protocol for animal handling and cells isolation (AR 2791) was approved by the Institutional Animal Care and Use Committee of the Medical University of South Carolina according to national legislation and guidelines.
Voltage-Clamp Recordings Cells were voltage-clamped in the whole-cell perforated patch configuration at a holding potential of −50 or −60 mV and depolarized to +10 mV to activate L-type $Ca^{2+}$ current ($I_{Ca}$) and $Ca^{2+}$-induced $Ca^{2+}$ release using a Dagan amplifier and pClamp software (Clampex 10.2). Borosilicate patch pipettes were prepared using a horizontal pipette puller (Model P-87; Sutter Instruments, Novato, Calif.). The pipettes had a resistance of 3-5 MΩ when filled with solution containing the following: 145 mM Cs-glutamate, 9 mM NaCl, 1 mM $MgCl_2$, and 10 mM HEPES (titrated to pH 7.2 with CsOH), and 0.69 mg/ml amphotericin B. The extracellular solution used during experiments contained the following: 137 mM NaCl, 5.4 mM KCl, 2 mM $CaCl_2$, 1 mM $MgCl_2$, 10 mM glucose, and 10 mM HEPES (titrated to pH 7.4 with NaOH). Rapid applications of 2.5 mM caffeine and pharmacological interventions were used to elucidate the action mechanism of xanthohumol. Most experiments were performed at 35° C. Voltage-clamp experiments testing dose response were performed at both 25° C. and 35° C.
Fluorescence Imaging of $Ca^{2+}$, ROS, and Xanthohumol A Noran Odyssey XL rapid two-dimensional laser-scanning confocal microscope (Noran Instruments, Madison, Wis.; Zeiss Axiovert TV135) was used with a x63 water-immersion objective, $\lambda_{ex}$=488 nm and $\lambda_{em}$>515 nm to measure kinetics and subcellular distribution of fluorescence signals according to known protocols. $Ca^{2+}$ was imaged after 20- to 30-minute incubation with fluo-4 AM (2 μM).

Figure 1:
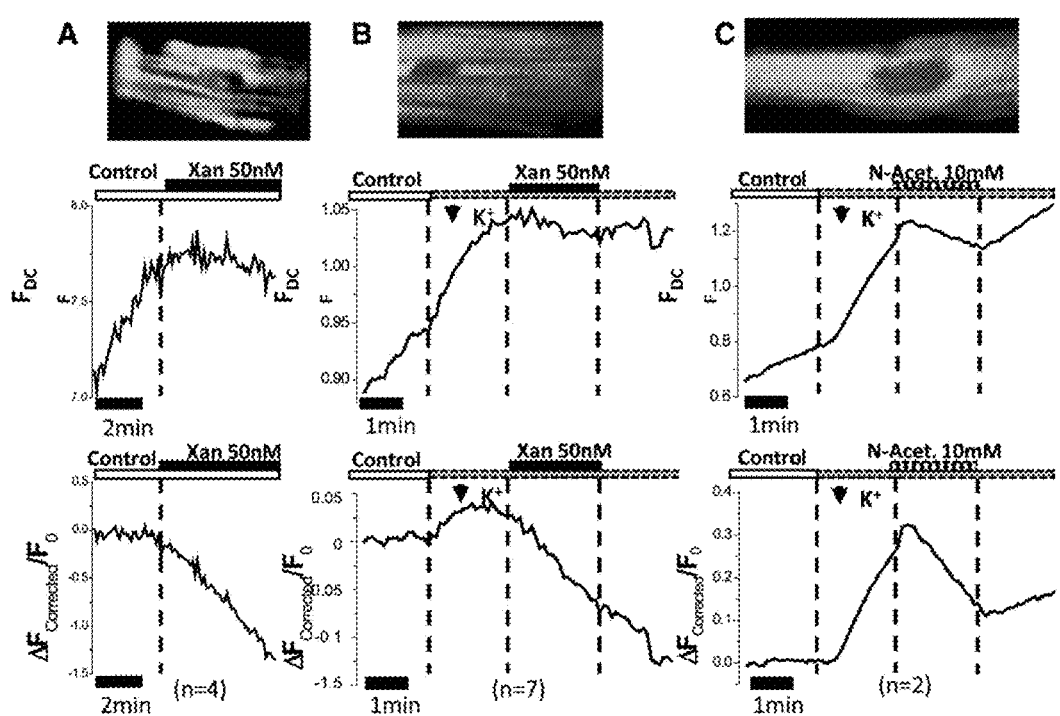
FIG. 1 illustrates the suppression of reactive oxygen species (ROS) levels by xanthohumol (50 nM) (A and B) and N-acetyl cysteine (10 mM) (C). Each panel includes a confocal image of ROS-dependent DCF fluorescence, FDCF, measured in a rat ventricular cardiomyocyte after 30-minute incubation with $H_2$DCFDA (5 µM, top image of each panel), changes in whole-cell FDCF after exposure to light, low $K^+$, and xanthohumol or N-acetyl cysteine (middle of each panel), and the fluorescence corrected to show normalized changes relative the initial 2- to 3-minute control interval ($\Delta F$ Corrected/$F_0$, bottom). (A) Suppression of baseline ROS production by xanthohumol. (B and C) Suppression of enhanced ROS production by xanthohumol (B) or N-acetyl cysteine (C) in cells challenged with low $K^+$ ($\downarrow K^+$, 5.4→1.5 mM). n, Indicates numbers of examined cells with similar responses.

ROS was measured by incubating cells with $H_2DCFDA$ (5 μM for 30 minutes), which is cleaved by esterases to form less permeant 2',7'-dichlorodihydrofluorescein that is then oxidized by free radical compounds to fluorescent 2',7'-dichlorofluorescein (DCF) as described previously. Fluorescence images of ROS were recorded at low fluorescence intensity and frame rate (about 1 Hz) and required considerable signal averaging (FIG. 1).

Figure 2:
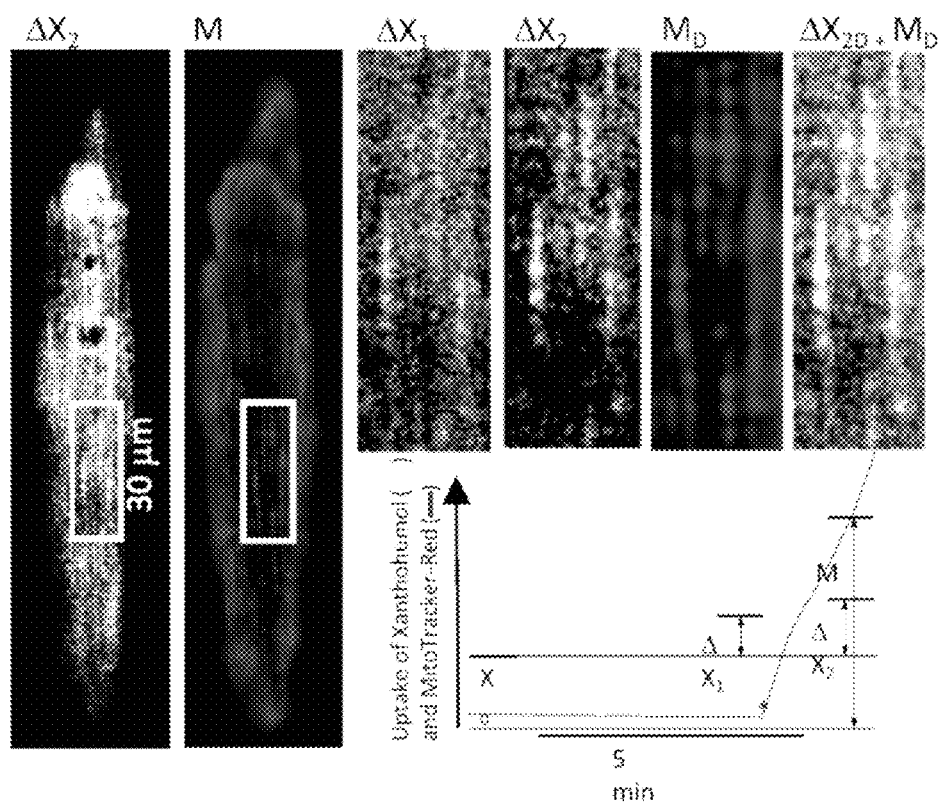
FIG. 2 illustrates uptake of xanthohumol and its co-localization with the mitochondrial marker MitoTracker-Red. As shown in the graph, MitoTracker-Red (1 mM, $\lambda_{ex}$=568 nm) was added 6 minutes (*) after xanthohumol (300 nM, $\lambda_{ex}$=405 nm) to guard against crossover between the fluorescence channels. Similarly, initial images of cellular autofluorescence ($X_0$) were subtracted from the later images ($\Delta X_1$, $\Delta X_2$, M) recorded in the xanthohumol channel. The expanded images from the boxed areas show typical mitochondrial distributions of xanthohumol before ($\Delta X_{1D}$) addition of MitoTracker-Red and afterward ($\Delta X_{2D}$) to allow comparison with a similarly timed detailed image of MitoTracker-Red fluorescence ($M_D$) as visualized by superimposition ($\Delta X_{2D}$+$M_D$). The images are shown without spatial averaging but with temporal averaging of 11 frames measured at 5-second intervals. Shown are records typical of four cells exposed to 300 nM xanthohumol.

The weak fluorescence of xanthohumol (50-1000 μM) allowed its uptake and subcellular mitochondrial distribution ($\lambda_{ex}$=405 nm) and co-localization with MitoTracker-Red ($\lambda_{ex}$=568 nm) to be monitored at 0.2 Hz in dual channel recordings with a LEICA microscope (TIRF DMI6000 B, 63x oil-immersion objective; Leica Microsystems, Buffalo Grove, Ill.) equipped with an Andor iXon3 camera (512×512 pixels of 0.254×0.254 μm², Belfast, UK) and operating in the epifluorescence mode (FIG. 2).

Figure 3:
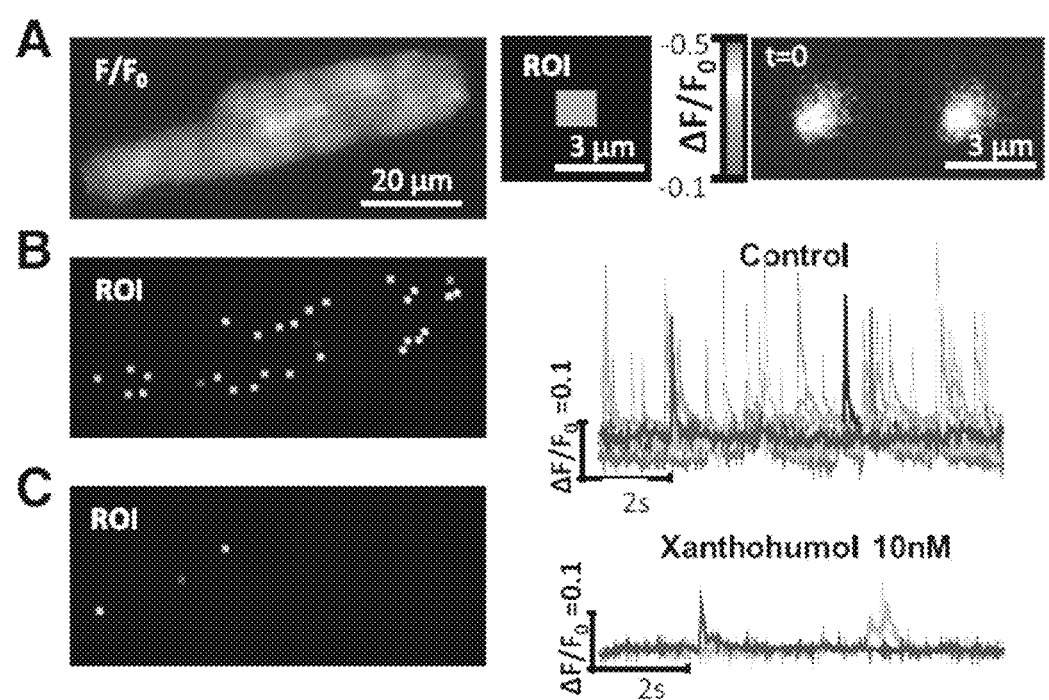
FIG. 3 illustrates suppression of spontaneous $Ca^{2+}$ sparks by xanthohumol (10 nm). (A) Baseline fluorescence ($F_0$) and region of interest (ROI) in relation to consecutive sample frames showing slowly fading $Ca^{2+}$ spark ($\Delta F/F_0$). (B and C) Locations (ROI) and time course of spontaneous $Ca^{2+}$ sparks recorded in 8-second intervals before (B) and after (C) addition of 10 nM xanthohumol. Epifluorescence measurements, 23 frames/s, 25° C., cell incubated with Fluo-4 AM.
Figure 4:
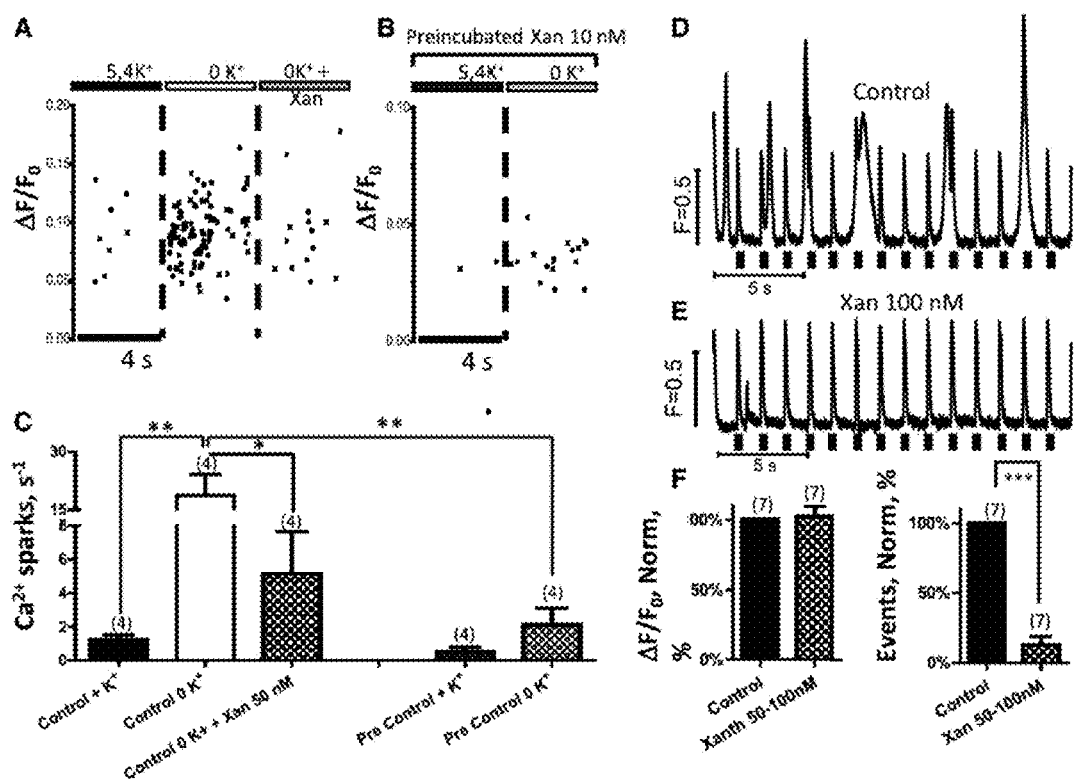

$Ca^{2+}$ sparks (Fluo-4, $\lambda_{ex}$=488 nm) were also measured with the LEICA DMI6000 microscope in the epifluorescence mode but now operating at 60-100 frames/s (FIG. 3, FIG. 4 (panels A-C); FIG. 5, FIG. 6, and FIG. 7); the average baseline fluorescence intensity ($F_0$) was calculated from several frames without indication of spontaneous $Ca^{2+}$ signals in the form of sparks or waves. Images were filtered by 2 pixel×2 pixel averaging. The amplitudes of the $Ca^{2+}$-dependent cellular fluorescence signals were quantified as $\Delta F/F_0$, where $\Delta F$ is the change in fluorescence measured within selected regions of interest. The time constant of decay of $Ca^{2+}$ transients (Tau) was estimated by approximation with a single exponential.
Global Intracellular $Ca^{2+}$ Measurements in Field-Stimulated and Voltage-Clamped Cells Whole-cell $Ca^{2+}$ transients occurring spontaneously or evoked electrically by field stimulation or voltage-clamp depolarizations or by rapid application of caffeine (2.5 mM for 0.5 or 1 second) were measured fluorometrically after incubating the cells in fluo-4 AM (2 μM) for 30 minutes. The dye was excited by 460 nm light from a LED-based illuminator (Prismatix, Modiin (lite, Israel), and $Ca^{2+}$-dependent fluorescent light (>500 nm) was detected with a photomultiplier tube that was placed behind a moveable, adjustable diaphragm, which served to limit the area of detection to the voltage-clamped cell. The cellular fluorescence signals ($\Delta F/F_0$) were normalized by dividing the changes in whole-cell fluorescence ($\Delta F$) with the baseline fluorescence ($F_0$).
Statistical Analysis Data are reported as means±S.E. Comparisons were done using one-way analysis of variance and the posterior Tukey's multiple comparison test, Bonferroni's multiple comparison test, or Newman-Keuls multiple comparison test. Also paired and unpaired t tests were realized when data requested. Levels of significance are indicated by one or more asterisks (*$P<0.05$, $P<0.01$, *$P<0.001$). Measured parameters (magnitude and Tau of $Ca^{2+}$ transients, the number of spontaneous $Ca^{2+}$ release events of $Ca^{2+}$ transients, and $I_{Ca}$ were generally normalized (Norm) relative to values measured under control conditions, that is, in the absence of xanthohumol and isoproterenol to eliminate variability from cell to cell.
Experimental Approach Effects of xanthohumol on cardiac $Ca^{2+}$ signaling were evaluated in enzymatically dispersed ventricular myocytes that were subjected to field stimulation or voltage-clamp depolarizations in the whole-cell, perforated patch configuration to activate $Ca^{2+}$ current ($I_{Ca}$) and SR $Ca^{2+}$ release.

The cells were incubated with fluo-4 AM for 30 minutes to allow fluorometric imaging of $Ca^{2+}$ sparks and measurements of whole-cell $Ca^{2+}$ transients. Rapid perfusion of caffeine was used to release, and SR $Ca^{2+}$ stores and assesses their size according to known methodology. Xanthohumol was tested in the range from 5 nM to 1 μM and was used routinely either with acute application of 50 nM drug or by incubation of cells in 10 nM xanthohumol-containing solutions for 30 minutes. All cells were first perfused with Tyrode's solution (137 mM NaCl, 10 mM HEPES, 10 mM glucose, 5.4 mM KCl, 2 mM CaCl, 1 mM MgCl) and thereafter were subjected to the following in the absence or presence of xanthohumol:

1) different rates of stimulation,
2) isoproterenol (100 nM),
3) solutions with little or no $K^+$ (0 or 1.5 mM), and
4) different temperatures (25° C. or 35° C.).

Each experimental condition was typically sustained for 2-8 minutes to achieve equilibration. To avoid cell damage due to continuous light exposure, recordings were generally performed for intervals of only 5-10 seconds, but repeated every minute. Cells challenged with isoproterenol or low $K^+$ typically developed more abundant spontaneous $Ca^{2+}$ sparks and interdispersed irregular whole-cell $Ca^{2+}$ transients, especially in the absence of xanthohumol.

Measurements of ROS were also carried out using the oxygen-radical sensitive dye 2',7'-dichlorofluorescein (DCF) (5 μM). The effect of the xanthohumol was compared with the antioxidant N-acetyl cysteine (10 mM).

Results

Xanthohumol Reduces ROS Generation

ROS production was evaluated from the rate of increase in DCF fluorescence in ventricular myocytes incubated with $H_2DCFDA$. Under these conditions, exposure of myocytes to xanthohumol (50 nM) reduced the slope of both uncompensated (FIG. 1 panel A, top image) and background-compensated (bottom), fluorescence signal consistent with the antioxidant property of xanthohumol. FIG. 1, at panels B and C, also shows comparison of xanthohumol to another antioxidant, N-acetyl cysteine, on a pair of ventricular myocytes, incubated with $H_2DCFDA$, and exposed to laser light and low $K^+$ solutions. The low $K^+$ solution-induced increase of the DCF signal was effectively suppressed by application of 50 nM xanthohumol, the effect of which persisted even after washout of xanthohumol. Similarly, but at higher concentration (10 mM), N-acetyl cysteine also suppressed the low $K^+$-induced increase of the DCF signal (FIG. 1, panel C), but its washout rapidly reversed the DCF signal, reflecting possibly different cellular compartmentation of N-acetyl cysteine and xanthohumol.

Intracellular Localization of Xanthohumol

Weak fluorescence of xanthohumol (300 nM, $\lambda_{ex}$=405 nm) was taken advantage of to determine its uptake (light trace) and mitochondrial compartmentation as seen in FIG. 2 in fluorescence images recorded in rat ventricular cell after 5 ($\Delta X_{D1}$), and 7 minutes ($\Delta X_2$, $\Delta X_{2D}$) both before and after addition (*) of the mitochondrial marker MitoTracker-Red (1 μM, $\lambda_{ex}$=405 nm, dark trace and images M and $M_D$). The boxed areas in panels $\Delta X_2$ and M were expanded to emphasize the detailed patterns of strings of mitochondria with sarcomeric spacing that were produced by both fluorescent compounds ($\Delta X_{D1}$, $\Delta X_{2D}$, $M_D$) and showed a high degree of co-localization ($\Delta X_{2D}+M_D$). After 6 minutes, the cellular fluorescence intensity produced by 300 and 100 nM xanthohumol was 130±14 (n=4) and 32±12 (n=2), respectively. In comparison, the cellular autofluorescence was 350±65 so that lower concentrations of xanthohumol were not reliably detected. Confocal imaging of pre-incubated cells confirmed the dose-dependent uptake and mitochondrial distribution of xanthohumol up to concentrations of about 30 μM (FIG. 8).

Spontaneously Triggered $Ca^{2+}$ Sparks and Waves are Suppressed by Xanthohumol The effects of brief exposures of xanthohumol on generation of $Ca^{2+}$ sparks and waves was explored in freshly isolated rat ventricular myocytes. In control cells that had a high baseline spontaneous $Ca^{2+}$ spark frequency, it was noted that acute application of 10 nM xanthohumol consistently reduced the spark frequency within 2 minutes of its application. FIG. 3 shows recordings of $Ca^{2+}$ sparks in an intact rat ventricular myocyte and strong suppression of their frequency by xanthohumol (panel C), as seen also in videos (images of which shown in FIG. 5). Continuous recordings showed that the effects of xanthohumol started to develop in less than 10 seconds (FIG. 9) whereas 5-second measurements repeated every minute showed the effects to stabilize within minutes (FIG. 6 and FIG. 7).

In myocytes showing lower frequencies of spontaneously triggered $Ca^{2+}$ sparks, reduction of $K^+$ or addition of isoproterenol consistently triggered $Ca^{2+}$ sparks and waves that often resulted in cytosolic $Ca^{2+}$ oscillations. Reduction of $K^+$ to values below about 1.5 mM generally increased the diastolic $Ca^{2+}$ levels and caused a 15-fold rise (p<0.005) in the number of $Ca^{2+}$ sparks (FIG. 4, panels A and C). In such cells, xanthohumol (50 nM) markedly decreased the frequency of $Ca^{2+}$ sparks evoked by withdrawal of extracellular $K^+$ (FIG. 4, panels A and C; FIG. 6). Higher concentrations of xanthohumol (50 nM) were necessary to reduce the enhanced frequency of spontaneously generated sparks on $K^+$ withdrawal. Cells subjected to longer periods of low $K^+$ often developed severe and irregular $Ca^{2+}$ oscillations that led to loss of excitability and were not further considered.

In another set of experiments, the frequency of spontaneously generated $Ca^{2+}$ sparks was measured in ventricular myocytes incubated for 30 minutes in control (5.4 mM $K^+$) solutions containing 10 nM xanthohumol. In such myocytes, spontaneously developed $Ca^{2+}$ oscillations or sparks were scarce (FIG. 4, panel B; FIG. 7). The incubating effect of xanthohumol was most prominent when subjecting the myocytes to $K^+$-free solutions (FIG. 4, panel B). That is, even though reduction of $K^+$ continued to increase the frequency of spontaneously occurring sparks leading to $Ca^{2+}$ oscillations in xanthohumol-incubated cells, the frequency of such events was significantly lower (p<0.005) than that measured in non-incubated cells (FIG. 4, panel C).

In a series of experiments carried at 35° C., the effect of xanthohumol in cells was examined where rapid electrical stimulation induced spontaneously triggered beats under control conditions (FIG. 4, panel D). In these cells, 100 nM xanthohumol suppressed significantly the spontaneously triggered beats without modifying the peak $\Delta F/F_0$, $F_0$, or decay time constant (Tau) of electrically triggered $Ca^{2+}$ transients (FIG. 4, panel F).

In a set of experiments exposed to 1.5 mM $K^+$ showing higher frequency of spontaneously triggered $Ca^{2+}$ oscillations (P<0.0001), although 1-5 μM tetrodotoxin failed to significantly reduce the frequency of spontaneously triggered events, 50 nM xanthohumol markedly reduced their frequency (FIG. 10). Washout of xanthohumol once again activated the low $K^+$-triggered increase in the frequency of $Ca^{2+}$ oscillations.

Effects of Xanthohumol on Spontaneously Triggered $Ca^{2+}$ Oscillations Evoked by Isoproterenol In ventricular myocytes that did not show spontaneously triggered activity under control conditions, isoproterenol often increased the number of spontaneous events that were recorded in the intervals between the electrically stimulated $Ca^{2+}$ transients (FIG. 11, panel A). Analysis of $Ca^{2+}$-signaling parameters in isoproterenol-treated myocytes (magnitude, Tau, number of spontaneously occurring $Ca^{2+}$ transients, and diastolic $Ca^{2+}$) showed that the amplitude of the $Ca^{2+}$ transients was increased by 50% (P=0.0464; FIG. 11, panel B), and its rate of relaxation enhanced by about 30% (FIG. 11, panel D) as the frequency of spontaneous events increased by 3- to 4-fold (FIG. 11, panel E). Co-application of isoproterenol with xanthohumol (50-300 nM) produced strong suppression of isoproterenol-triggered spontaneous events (FIG. 11, panel E) without having a significant effect on various parameters of $Ca^{2+}$ transients (FIG. 11, panels B-D). Thus, it appears that xanthohumol suppressed the arrhythmogenic effects of β-adrenergic agonists without suppressing their inotropic or relaxant effects.

Dose-Dependent Effects of Xanthohumol

Using a similar approach, the concentration-dependent effects of xanthohumol were examined on amplitude and rate of decay of $Ca^{2+}$ transients at 35° C. (FIG. 12). Each myocyte was exposed to only one concentration of xanthohumol for a period of 3 minutes to prevent progressive effects resulting from intracellular accumulations of xanthohumol. The parameters evaluated the following: normalized $\Delta F$, $F_0$, and the time constant of decay $Ca^{2+}$ transient, Tau (FIG. 12, panels A and C), showed that the application of xanthohumol (50-100 nM) produced a slight increase in the normalized $\Delta F$ or $F_0$ (statistically insignificant), in the range of 10-300 nM, without much change on Tau of relaxation, until toxic concentrations (about 1 mM) were reached (FIG. 12, panels A-C).

Effect of Xanthohumol on Modulation of $Ca^{2+}$ Transients by High-Frequency Electrical Stimulation As is known, electrically triggered $Ca^{2+}$ transients are enhanced in response to higher frequency of stimulation. FIG. 13 shows an increase in the peak amplitude (FIG. 12, panels A and C) and a decrease in the Tau value of relaxation of the $Ca^{2+}$ transient (FIG. 12, panel B) in response to acute increase in the frequency of stimulation from 0.5 to 2 Hz. Quantification of data suggests 41.18%±9.743 (n=9) increase in $Ca^{2+}$-transient peaks following a 30-second train of high-frequency stimulation, compared with 12.14%±2.662 (n=4) in 50-100 nM xanthohumol, and a 5.002%±0.6667 in cells exposed to xanthohumol and isoproterenol (100 nM; FIG. 12, panel C). Thus, it appears that enhancement of $Ca^{2+}$ uptake by isoproterenol or its suppression by xanthohumol interferes with the beat-dependent enhancement of $Ca^{2+}$ transients.

Xanthohumol Effects on the SR $Ca^{2+}$ Stores and its Rate of Refilling

The aim of this set of experiments was to examine the effect of the xanthohumol on the SR $Ca^{2+}$ content and its recirculation. FIG. 14 compares the magnitude of $Ca^{2+}$ transients in electrically stimulated cells paced at 0.5 Hz to $Ca^{2+}$ transient that was produced when one stimulus was replaced by a rapid application of 2.5 mM caffeine for 1 second. The magnitude of $Ca^{2+}$ release produced by caffeine was taken as a measure of total $Ca^{2+}$ content of the SR and is quantified in FIG. 14. $\Delta F/F$ signal was significantly reduced in presence of xanthohumol (FIG. 14, panel B), but the fractional $Ca^{2+}$ release was not significantly reduced (FIG. 14, panel C). The slight suppressive effect of xanthohumol on electrically- or caffeine-triggered $Ca^{2+}$ release did not significantly alter the isoproterenol-potentiating effect on $\Delta F/F$ or on the fractional $Ca^{2+}$ release (FIG. 14, panels B and C), suggesting that xanthohumol-suppressive effects are not likely to be mediated through suppression of calcium-induced calcium release (CICR) or masking of protein kinase A phosphorylation sites. The slight increase in diastolic $Ca^{2+}$ levels (statistically insignificant) caused by xanthohumol was also reversed by isoproterenol (FIG. 14, panel D). It was concluded that xanthohumol suppresses slightly the $Ca^{2+}$ content of the SR, but this effect was fully reversed by isoproterenol.

To probe the effect of xanthohumol on recirculation of SR $Ca^{2+}$ and its refilling following depletion of its content by caffeine, the rate of recovery of electrically triggered $Ca^{2+}$ transients back to control levels was quantified as a measure of refilling of the SR store. FIG. 15, panel A shows almost complete recovery (91.2%±2.64, n=30) of $Ca^{2+}$ transients in control cells after seventh electrically triggered beat, when compared with triggered $Ca^{2+}$ transients prior to application of caffeine (I). FIG. 15, panel D also shows that xanthohumol (50 nM) reduced the peak of the triggered $Ca^{2+}$ transient paced at 0.5 Hz (I) by 22.66%, and isoproterenol increased it by 74.12%. Xanthohumol also significantly reduced the rate of refilling of the SR (FIG. 15, panel B), but the effect was fully reversed by isoproterenol (compare FIG. 15, panels A-C). Percent recovery of the seventh pulse after caffeine was 91.2%±2.64 (n=30) in control, compared with 70.52%±8.13 (n=11) in 50-100 nM xanthohumol, and 95.37%±1.18 (n=12) in xanthohumol plus isoproterenol (FIG. 15, panel E).

FIG. 15, panels D-F, compares the effects of xanthohumol on the rate of relaxation of $Ca^{2+}$ transients in control and isoproterenol-treated ventricular myocytes during recovery phase following depletion of SR stores by caffeine. Time constant of relaxation (Tau) for the second and seventh pulse following the SR depletion by caffeine was significantly reduced by 10.33% and 5.44%, respectively, in control solutions. In presence of xanthohumol, the modulatory effect on the uptake kinetics produced following $Ca^{2+}$ release by caffeine was completely suppressed. Once again, isoproterenol recovered the modulatory effect of caffeine-induced $Ca^{2+}$ release on the rate of relaxation of second and to a lesser extent the seventh beat following recovery from caffeine-induced rise in cytosolic $Ca^{2+}$. The data therefore suggest that xanthohumol may interfere with rate of uptake of $Ca^{2+}$ by a mechanism that can be overridden by isoproterenol.

Temperature Dependence of Xanthohumol Effects

The effects of xanthohumol on $Ca^{2+}$ signaling parameters was compared using concentrations ranging between 1 nM and 1 μM. The experiments were carried out under perforated patch conditions both at room temperature and 35° C. Ventricular myocytes incubated in fluo-4 AM were activated by 100-ms depolarizing pulses from −50 to 10 m versus at room temperature. $Ca^{2+}$ current was suppressed by xanthohumol when the concentrations of the drug exceeded 100 nM (FIG. 16, panel A). In sharp contrast at 35° C., 100-300 nM xanthohumol concentrations significantly increased the $Ca^{2+}$ current. Unexpectedly, 10 nM xanthohumol, at room temperature, which had little or no effect on $I_{Ca}$, significantly suppressed $Ca^{2+}$ transients (compare FIG. 16, panels A and B). At room temperatures, xanthohumol also slowed the kinetics of relaxation of $Ca^{2+}$ transients, as it suppressed its peak, at concentrations exceeding 50 nM (FIG. 16, panels B and C; P<0.001). The strong suppressive effects of xanthohumol in reducing the peak and slowing the decay of the $Ca^{2+}$ transients were significantly reduced at 35° C., such that only concentrations exceeding 300 nM had significant effects on $\Delta F/F$ or rate of their decay (FIG. 16, panels E and F). It was concluded that higher metabolic states of myocytes, induced by higher temperatures and adrenergic stimulation, reduce the inhibitory effects of xanthohumol on $Ca^{2+}$ transients.

While certain embodiments of the disclosed subject matter have been described using specific terms, such description is for illustrative purposes only, and it is to be understood that changes and variations may be made without departing from the spirit or scope of the subject matter.

What is claimed is:

1. A method for modulating $Ca^{2+}$ signaling in a cardiac myocyte, the method comprising delivering xanthohumol to the cardiac myocyte such that the xanthohumol contacts the cardiac myocyte at a concentration of from about 5 nM to about 1 μM.

2. The method of claim 1, wherein the xanthohumol is delivered to the cardiac myocyte such that the xanthohumol contacts the cardiac myocyte at a concentration of from about 5 nM to about 50 nM.

3. The method of claim 1, wherein the xanthohumol is delivered to the cardiac myocyte such that the xanthohumol contacts the cardiac myocyte at a concentration of from about 50 nM to about 100 nM.

4. The method of claim 1, wherein the method suppresses aberrant spontaneous activity of a ryanodine receptor 2 of the cardiac myocyte.

5. The method of claim 1, wherein the method reduces the rate of relaxation of $Ca^{2+}$ transients.

6. The method of claim 5, wherein the rate of relaxation of $Ca^{2+}$ transients is suppressed without suppressing $Ca^{2+}$ current in the cardiac myocyte.

7. The method of claim 1, wherein the method suppresses $Ca^{2+}$ content of the sarcoplasmic reticulum.

8. The method of claim 1, wherein the xanthohumol is delivered to the cardiac myocyte in conjunction with a β-adrenergic agonist.

9. The method of claim 8, wherein the β-adrenergic agonist comprises isoproterenol.

10. A method for modulating $Ca^{2+}$ signaling in a cardiac myocyte, the method comprising delivering xanthohumol to the cardiac myocyte during or following subjection of the cardiac myocyte to $Ca^{+2}$ overload conditions, such that the xanthohumol contacts the cardiac myocyte at a concentration of from about 5 nM to about 1 μM.

11. The method of claim 10, wherein the xanthohumol is delivered to the cardiac myocyte such that the xanthohumol contacts the cardiac myocyte at a concentration of from about 5 nM to about 100 nM.

12. The method of claim 10, wherein the $Ca^{2+}$ overload conditions comprise a low potassium environment.

13. The method of claim 10, wherein the $Ca^{2+}$ overload conditions comprise an electrical stimulation.

14. The method of claim 10, wherein the $Ca^{2+}$ overload conditions comprise exposure to a cardiac stimulating chemical.

15. The method of claim 14, wherein the cardiac stimulating chemical comprises a β-adrenergic agonist or caffeine.

16. The method of claim 14, wherein the cardiac stimulating chemical comprises isoproterenol.

\* \* \* \* \*